US012588839B2

(12) United States Patent
Tanaka et al.

(10) Patent No.: US 12,588,839 B2
(45) Date of Patent: Mar. 31, 2026

(54) COMPONENT CONCENTRATION MEASURING DEVICE

(71) Applicant: NTT, Inc., Tokyo (JP)

(72) Inventors: Yujiro Tanaka, Tokyo (JP); Daichi Matsunaga, Tokyo (JP); Masahito Nakamura, Tokyo (JP); Michiko Seyama, Tokyo (JP)

(73) Assignee: NTT, INC., Tokyo (JP)

( * ) Notice: Subject to any disclaimer, the term of this patent is extended or adjusted under 35 U.S.C. 154(b) by 823 days.

(21) Appl. No.: 17/417,515

(22) PCT Filed: Dec. 10, 2019

(86) PCT No.: PCT/JP2019/048254
§ 371 (c)(1),
(2) Date: Jun. 23, 2021

(87) PCT Pub. No.: WO2020/137515
PCT Pub. Date: Jul. 2, 2020

(65) Prior Publication Data
US 2022/0110556 A1 Apr. 14, 2022

(30) Foreign Application Priority Data
Dec. 25, 2018 (JP) ................................. 2018-240791

(51) Int. Cl.
*A61B 5/145* (2006.01)
*A61B 5/00* (2006.01)
(52) U.S. Cl.
CPC ........ *A61B 5/14532* (2013.01); *A61B 5/0095* (2013.01); *A61B 5/6816* (2013.01); *A61B 5/6838* (2013.01)

(58) Field of Classification Search
CPC . A61B 5/14532; A61B 5/0095; A61B 5/6816; A61B 5/6838
See application file for complete search history.

(56) References Cited

U.S. PATENT DOCUMENTS 6,172,743 B1 * 1/2001 Kley ................... A61B 5/14532
356/39
2004/0162470 A1 * 8/2004 Tu ....................... A61B 5/14532
600/316

(Continued)

FOREIGN PATENT DOCUMENTS

JP        2006326224 A    12/2006
JP        2007229320 A    *   9/2007
JP        2010104858 A    5/2010

Primary Examiner — Rene T Towa
Assistant Examiner — Ari S Padda
(74) Attorney, Agent, or Firm — Slater Matsil, LLP

(57) ABSTRACT

A first holding member and a second holding member are arranged so as to sandwich a measurement site of a measurement subject, and are capable of clamping the measurement site. A light beam emitted from a light emitting unit is guided to the first holding member by an optical fiber, passes through an optical system, is reflected by a reflection unit, and is then incident on the measurement site. A detection unit housed in the second holding member detects a photoacoustic signal generated in the measurement site irradiated with the light beam emitted from the light emitting unit. A matching member is arranged between the second holding member and the measurement site, and is in contact with the measurement site.

11 Claims, 6 Drawing Sheets

(56) References Cited

U.S. PATENT DOCUMENTS

| | | | |
|---|---|---|---|
| 2012/0238859 A1* | 9/2012 | Tokita | A61B 5/0095 |
| | | | 600/407 |
| 2013/0123590 A1* | 5/2013 | Naganuma | A61B 5/6826 |
| | | | 600/316 |
| 2015/0005613 A1* | 1/2015 | Kim | G01N 29/2418 |
| | | | 600/407 |

* cited by examiner

COMPONENT CONCENTRATION MEASURING DEVICE

CROSS-REFERENCE TO RELATED APPLICATIONS

This application is a national phase entry of PCT Application No. PCT/JP2019/048254, filed on Dec. 10, 2019, which claims priority to Japanese Application No. 2018-240791, filed on Dec. 25, 2018, which applications are hereby incorporated herein by reference.

TECHNICAL FIELD

The present invention relates to a component concentration measuring device, and more specifically relates to a component concentration measuring device for non-invasively measuring the concentration of a component such as glucose in blood.

BACKGROUND

Technical Field

The present invention relates to a component concentration measuring device, and more specifically relates to a component concentration measuring device for non-invasively measuring the concentration of a component such as glucose in blood.

Background Art

Knowing (measuring) the blood glucose level is very important when determining an insulin dosage for a person with diabetes, preventing diabetes, and so on. The blood glucose level is the concentration of glucose in blood, and photoacoustics is a well-known method for measuring the concentration of this type of component (see PTL 1).

When a living body is irradiated with a certain amount of light (electromagnetic waves), the emitted light is absorbed by molecules of the living body. For this reason, measurement target molecules in the portion irradiated with light are locally heated and expand, thus emitting acoustic waves. The pressure of such acoustic waves is dependent on the quantity of molecules that absorb the light. Photoacoustics is a method of measuring a molecular quantity in a living body by measuring such acoustic waves (a photoacoustic signal). Acoustic waves are pressure waves that propagate in a living body and have a characteristic of undergoing less diffusion than electromagnetic waves, and therefore photoacoustics can be said to be suited to the measurement of a blood component in a living body.

Photoacoustic measurement makes it possible to continuously monitor the glucose concentration in blood. Furthermore, photoacoustic measurement does not require a blood sample, and does not cause the measurement subject discomfort.

CITATION LIST

Patent Literature

PTL 1 Japanese Patent Application Publication No. 2010-104858

SUMMARY

Technical Problem

When the above-described photoacoustic measurement is performed on a human body, an acoustic wave measurement unit is brought into contact with a target portion of the human body. In this type of measurement, a detection unit is attached to a person's ear lobe, for example. In this example, the measurement site is clamped by a pair of holding members, one of the holding members emits a light beam onto the measurement site, and the detection unit included in the other holding member detects a photoacoustic signal. The two holding members are coupled by a coupling portion that extends through a coil spring that biases the holding members in the closing direction. The measurement site is clamped between the two holding member by the closing direction force applied by the coil.

As described above, due to clamping the measurement site with the holding members, a measurement unit such as the detection unit is attached so as to be pressed against the measurement site, but the above-described attachment state changes due to body movement. When the attachment state changes, the area of contact between the detection unit and the measurement site changes, and the detected photoacoustic signal changes, thus causing measurement error to occur.

Embodiments of the present invention were achieved in order to solve the foregoing problems, and an object of the present invention is to suppress measurement error caused by body movement when measuring the concentration of a component such as glucose in a human body using photoacoustics.

Means for Solving the Problem

A component concentration measuring device according to an aspect of embodiments of the present invention includes: a pair of holding members including a first holding member and a second holding member that are configured to clamp a measurement site of a measurement subject; a light emitting unit configured to emit a light beam having a wavelength absorbed by a measurement target substance from the first holding member toward the measurement site; a detection unit that is housed in the second holding member and configured to detect a photoacoustic signal generated by the measurement site when irradiated with the light beam; and a matching member that is configured to be arranged between the second holding member and the measurement site, and is configured to perform acoustic matching between the detection unit and the measurement site by undergoing elastic deformation with a constant elastic modulus while in contact with the measurement site.

In an example of a configuration of the component concentration measuring device, the matching member fills a gap between the second holding member and the measurement site when the measurement site is clamped between the pair of holding members.

In an example of a configuration of the component concentration measuring device, the component concentration measuring device further includes a resonator configured to cause the photoacoustic signal to resonate, the resonator being constituted by a first reflection unit that is arranged between the first holding member and the measurement site and has a first reflection surface configured to reflect the acoustic signal while allowing the light beam to pass, and a second reflection unit that is arranged between the second holding member and the measurement site and has a second reflection surface configured to reflect the photoacoustic signal, and the matching member fills a gap between the second reflection unit and the measurement site when the measurement site is clamped between the pair of holding members.

In an example of a configuration of the component concentration measuring device, the first reflection surface and the second reflection surface are parallel with each other.

In an example of a configuration of the component concentration measuring device, the first reflection surface faces the measurement site, and the first reflection unit further includes a first contact surface that faces the first holding member and is in contact with a light emitting end of the light emitting unit, and a void formed between the first reflection surface and the first contact surface.

In an example of a configuration of the component concentration measuring device, the second reflection surface faces the measurement site, and the second reflection unit includes a second contact surface that faces the second holding member and is in contact with a detection surface, which faces the measurement site, of the detection unit housed in the second holding member, and a void formed between the second reflection surface and the second contact surface.

In an example of a configuration of the component concentration measuring device, the matching member is constituted by a sponge made of a synthetic resin.

In an example of a configuration of the component concentration measuring device, the component concentration measuring device further includes a concentration calculation unit configured to obtain a concentration of the substance with use of the photoacoustic signal.

In an example of a configuration of the component concentration measuring device, the substance is glucose, and the light emitting unit emits a light beam having a wavelength absorbed by glucose.

Effects of Embodiments of the Invention

As described above, according to embodiments of the present invention, the matching member performs acoustic matching with the measurement site by undergoing elastic deformation with a constant elastic modulus, thus obtaining an excellent effect of making it possible to suppress measurement error caused by body movement when measuring the concentration of a component by photoacoustics.

DETAILED DESCRIPTION OF ILLUSTRATIVE EMBODIMENTS

The following describes a component concentration measuring device according to embodiments of the present invention.

First Embodiment

Figure 1:
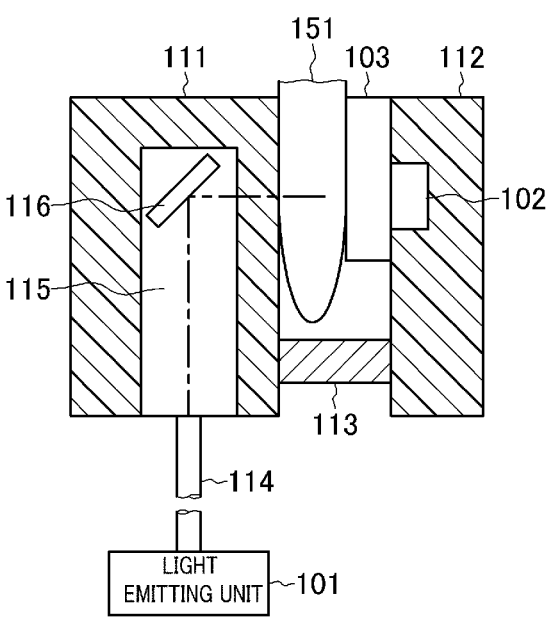
FIG. 1 is a configuration diagram showing a configuration of a portion of a component concentration measuring device according to a first embodiment of the present invention.
Figure 2:
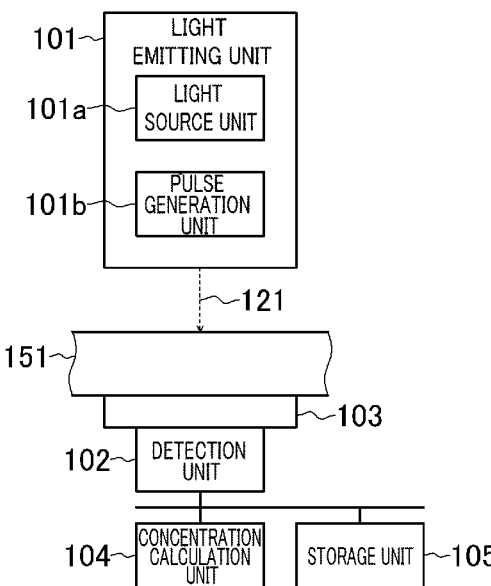
FIG. 2 is a configuration diagram showing a configuration of a portion of the component concentration measuring device according to the first embodiment of the present invention.

First, a component concentration measuring device according to a first embodiment of the present invention will be described with reference to FIGS. 1 and 2. This component concentration measuring device includes a light emitting unit 101, a detection unit 102, a matching member 103, a concentration calculation unit 104, a storage unit 105, a first holding member in, and a second holding member 112.

The first holding member in and the second holding member 112 are arranged so as to be located on opposite sides of a measurement site 151 of a measurement subject, and are capable of clamping the measurement site 151. The first holding member in and the second holding member 112 are made of plastic and shaped as a rectangular parallelepiped, for example. The first holding member in and the second holding member 112 are coupled to each other by a coupling portion 113. A coil spring (not shown) that biases the first holding member in and the second holding member 112 in a closing direction is fitted around the coupling portion 113. The measurement site 151 is sandwiched between the first holding member in and the second holding member 112 due to the closing direction force applied by the coil spring. The measurement site 151 is an ear lobe, for example.

The light emitting unit 101 generates a light beam 121 having a wavelength that is absorbed by the measurement target substance, and the generated light beam 121 is emitted from the first holding member in toward the measurement site 151. For example, in the case where the measurement target substance is glucose in blood, the light emitting unit 101 includes a light source unit 101a that generates a light beam 121 having a wavelength that is absorbed by glucose, and a pulse generation unit 101b that converts the light beam 121 generated by the light source into pulsed light that has a pre-set pulse width.

In this example, the light beam emitted from the light emitting unit 101 is introduced into the first holding member 111 by an optical fiber 114. The introduced light beam passes through an optical system 115 provided inside the first holding member in, and is then reflected by a reflection unit 116. The light beam reflected by the reflection unit 116 is then incident on the measurement site 151.

Note that glucose exhibits a property of absorbing light in wavelength bands near 1.6 μm and 2.1 μm (see PTL 1). If glucose is the measurement target substance, the light beam 121 emitted by the light emitting unit 101 is a light beam having a pulse width of 0.02 seconds or longer.

The detection unit 102 is housed in the second holding member 112. The detection unit 102 detects a photoacoustic signal from the measurement site 151 that was irradiated with the light beam 121. The detection unit 102 can be a unit that employs a piezoelectric effect or an electrostrictive effect (e.g., a crystal microphone, a ceramic microphone, or a ceramic ultrasonic sensor), a unit that employs electromagnetic induction (e.g., a dynamic microphone or a ribbon microphone), a unit that employs an electrostatic effect (e.g., a condenser microphone), or a unit that employs magnetostriction (e.g., a magnetostrictive vibrator). For example, in the case of employing a piezoelectric effect, the unit includes a crystal made of a frequency flat-type electrostrictive element (ZT) or PVDF (polyvinylidene fluoride). The detection unit 102 can be constituted by a PZT that includes an FET (Field Effect Transistor) amplifier.

When the measurement site 151 is sandwiched between the first holding member in and the second holding member 112, the detection unit 102 detects a photoacoustic signal generated by a light beam that was incident on the measurement site 151. At this time, the detection unit 102 may store the photoacoustic signal in the storage unit 105 along with time information indicating the time when the photoacoustic signal was measured.

The matching member 103 is arranged between the second holding member 112 and the measurement site 151 and performs acoustic matching between the detection unit 102 and the measurement site 151 by undergoing elastic deformation with a constant elastic modulus while in contact with the measurement site 151. In the first embodiment, the matching member 103 fills the gap between the second holding member 112 and the measurement site 151. The matching member 103 is shaped as a circular or rectangular plate in a plan view.

Figure 3:
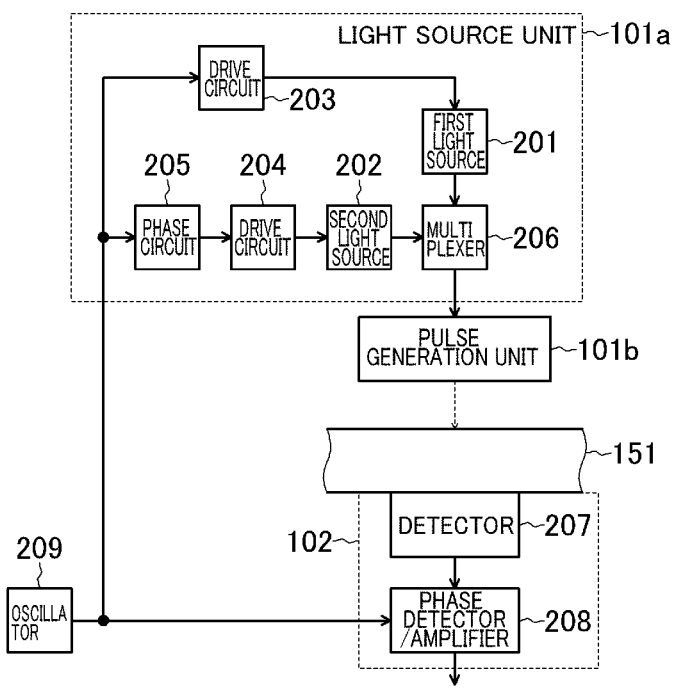
FIG. 3 is a configuration diagram showing a more detailed configuration of the component concentration measuring device according to the first embodiment of the present invention.

The following is a more detailed description of the light emitting unit 101 and the detection unit 102 with reference to FIG. 3. First, the light source unit 101*a* includes a first light source 201, a second light source 202, a drive circuit 203, a drive circuit 204, a phase circuit 205, and a multiplexer 206. Also, the detection unit 102 includes a detector 207, a phase detector/amplifier 208, and an oscillator 209.

The oscillator 209 is connected to the drive circuit 203, the phase circuit 205, and the phase detector/amplifier 208 by signal lines. The oscillator 209 transmits signals to the drive circuit 203, the phase circuit 205, and the phase detector/amplifier 208.

The drive circuit 203 receives the signal transmitted by the oscillator 209 and supplies drive power to the first light source 201 so as to cause the first light source 201 to emit light whose intensity has been modulated in synchronization with the frequency of the received signal. The first light source 201 is a semiconductor laser, for example.

The phase circuit 205 receives the signal transmitted by the oscillator 209, applies a 180-degree phase change to the received signal, and transmits the resulting signal to the drive circuit 204 via a signal line.

The drive circuit 204 receives the signal transmitted by the phase circuit 205 and supplies drive power to the second light source 202 so as to cause the second light source 202 to emit light whose intensity has been modulated in synchronization with the frequency of the received signal and the 180-degree phase changed signal received from the phase circuit 205. The second light source 202 is a semiconductor laser, for example.

The first light source 201 and the second light source 202 output light beams that have mutually different wavelengths, and the output light beams are each guided to the multiplexer 206 by an optical wave transmitting means. The wavelengths of the first light source 201 and the second light source 202 are set such that the wavelength of one of the light beams is a wavelength absorbed by glucose and the wavelength of the other light beam is a wavelength absorbed by water. Also, the wavelengths are set so as to have equivalent extents of absorption.

The light beam output by the first light source 201 and the light beam output by the second light source 202 are multiplexed into one light beam in the multiplexer 206, and the one light beam is then incident on the pulse generation unit 101*b*. The pulse generation unit 101*b* can be constituted by a light chopper, for example. Upon receiving the light beam, the pulse generation unit 101*b* emits the incident light beam toward the measurement site 151 as pulsed light that has a predetermined pulse width.

The detector 207 detects the photoacoustic signal generated at the measurement site 151, converts the photoacoustic signal into an electrical signal, and transmits the electrical signal to the phase detector/amplifier 208 via a signal line. The phase detector/amplifier 208 receives a synchronization signal necessary for synchronous detection from the oscillator 209, receives the electrical signal that is proportional to the photoacoustic signal from the detector 207, performs synchronous detection, amplification, and filtering, and outputs an electrical signal that is proportional to the photoacoustic signal. The processed electrical signal (photoacoustic signal) is then stored in the storage unit 105 along with information indicating the time when the electrical signal was measured.

The intensity of the signal output by the phase detector/amplifier 208 is proportional to the quantities of light absorbed by components (glucose and water) at the measurement site 151 when irradiated with the light beams output by the first light source 201 and the second light source 202, and therefore the intensity of the signal is proportional to the quantities of such components at the measurement site 151. The concentration calculation unit 104 therefore obtains the quantity (concentration) of a measurement-target substance (glucose) component in the blood at the measurement site 151 based on a measured value of the intensity of the output signal (photoacoustic signal).

As described above, two beams of light that have been subjected to intensity modulation using signals that have the same frequency are used in order to eliminate the influence of the non-uniformity of frequency characteristics when using multiple light beams, which is a problem that occurs in the case where intensity modulation is performed using signals that have different frequencies.

However, non-linear absorption coefficient dependence of photoacoustic signals, which is a problem in measurement using photoacoustics, can be resolved by performing measurement using light beams that have different wavelengths but have the same absorption coefficient as described above (see PTL 1).

In the component concentration measuring device of the first embodiment described above, the matching member 103 is sandwiched between the second holding member 112 and the measurement site 151. The first holding member in and the second holding member 112, which are coupled by the coupling portion 113 that extends through the coil spring, clamp the matching member 103 and the measurement site 151 with an appropriate force for preventing falling, and the matching member 103 is pressed against the measurement site 151 with a constant force. The matching member 103, which is pressed against the measurement site 151 in this way, undergoes elastic deformation with a constant elastic modulus while in close contact with the measurement site 151. For this reason, even if the measurement site 151 undergoes deformation due to body movement or the like, the area of contact between the matching member 103 and the measurement site 151 always stays constant.

The photoacoustic waves detected by the detection unit 102 change according to the radiation direction. For this reason, in order to perform accurate and highly-reproducible measurement, it is necessary to keep a constant area of contact as described above. If the matching member 103 is not used, the detection surface of the detection unit 102, which does not undergo deformation, comes into contact with the measurement site 151. In this case, even if the detection unit 102 is pressed against the measurement site 151 with a constant force, the area of contact changes if the measurement site 151 undergoes deformation due to body movement or the like. In contrast, the area of contact is always kept constant as described above by using the matching member 103, thus making it possible to perform accurate and highly-reproducible photoacoustic measurement.

The matching member 103 can be constituted by a porous body (sponge) made of an elastomer, a gel, or a synthetic resin, for example. For example, it is possible to calculate a hole density that obtains a predetermined elastic modulus through analysis by simulation, and form the matching member 103 from a porous body that reflects the simulation results.

Figure 4:
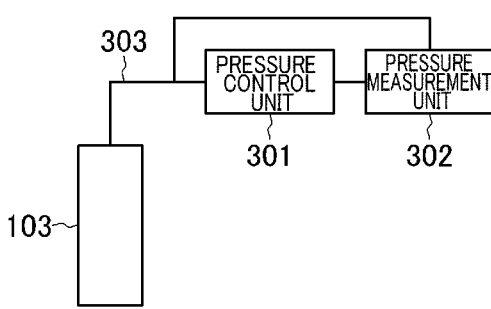
FIG. 4 is a configuration diagram showing a configuration of a portion of the component concentration measuring device according to the first embodiment of the present invention.

Also, as shown in FIG. 4, a configuration is possible in which the matching member 103 has a balloon-shaped structure, and the internal pressure is always kept constant by a pressure control unit 301 and a pressure measurement unit 302. The pressure measurement unit 302 measures the pressure in a tube 303 that extends from the interior of the matching member 103 to the pressure control unit 301. The pressure control unit 301 controls the internal pressure of the matching member 103 such that the pressure measured by the pressure measurement unit 302 is always constant.

Second Embodiment

Figure 5:
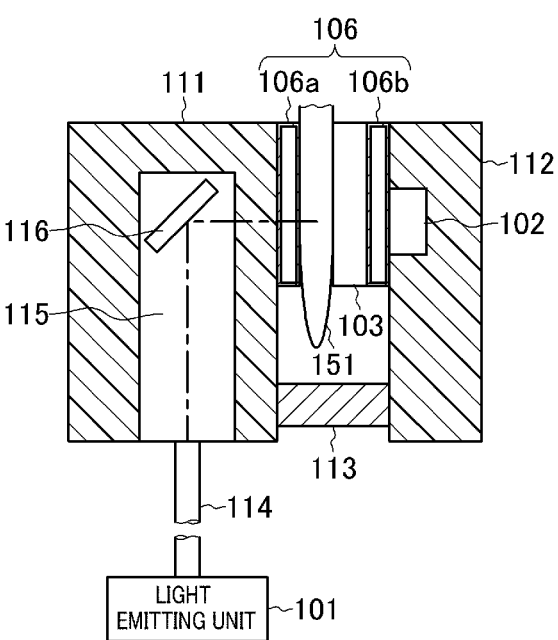
FIG. 5 is a configuration diagram showing a configuration of a portion of a component concentration measuring device according to a second embodiment of the present invention.
Figure 6:
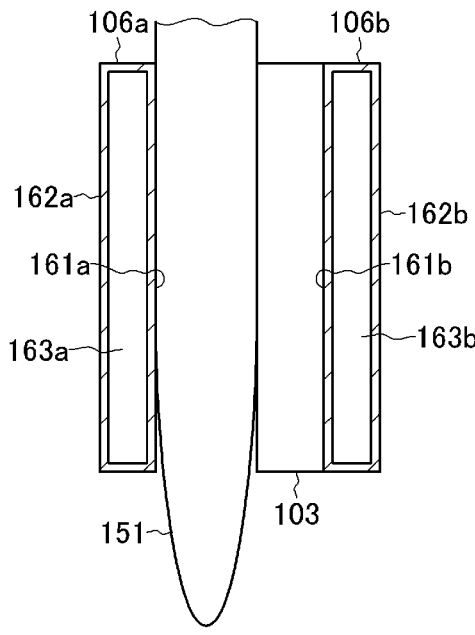
FIG. 6 is a configuration diagram showing a configuration of a portion of the component concentration measuring device according to the second embodiment of the present invention.

The following describes a second embodiment of the present invention with reference to FIGS. 5 and 6. This component concentration measuring device includes the light emitting unit 101, the detection unit 102, the matching member 103, the concentration calculation unit 104, the storage unit 105, the first holding member in, and the second holding member 112. The configurations of these constituent elements are similar to those in the first embodiment described above.

In the second embodiment, a resonator 106 that causes the photoacoustic signal to resonate is provided so as to sandwich the measurement site 151. The resonator 106 is constituted by a first reflection unit 106a and a second reflection unit 106b. The first reflection unit 106a is arranged between the first holding member iii and the measurement site 151, and has a first reflection surface 161a that reflects the photoacoustic signal while allowing the light beam to pass. The second reflection unit 106b is arranged between the second holding member 112 and the measurement site 151, and has a second reflection surface 161b that reflects the photoacoustic signal. The first reflection surface 161a and the second reflection surface 161b are parallel with each other. The matching member 103 fills the gap between the second reflection unit 106b and the measurement site 151 when the measurement site 151 is sandwiched between the first holding member in and the second holding member 112.

The first reflection surface 161a and the second reflection surface 161b face the measurement site 151. The first reflection unit 106a has a first contact surface 162a that faces the first holding member in and is in contact with the light emitting end of the light emitting unit 101. The second reflection unit 106b has a second contact surface 162b that is in contact with the detection surface of the detection unit 102 that faces the measurement site 151. Also, in this example, a void 163a is formed between the first reflection surface 161a and the first contact surface 162a. Similarly, a void 163b, is formed between the second reflection surface 161b and the second contact surface 162b.

As described above, a photoacoustic signal is generated when the light beam reflected by the reflection unit 116 is incident on the measurement site 151 clamped between the first reflection unit 106a and the second reflection unit 106b, and the photoacoustic signal is reflected between the first reflection surface 161a and the second reflection surface 161b. If the first reflection surface 161a and the second reflection surface 161b are separated by a gap at which the generated photoacoustic signal resonates (vibrates sympathetically), the photoacoustic signal resonates due to the resonator 106 constituted by the first reflection unit 10a and the second reflection unit 106b, thus obtaining a higher sound pressure. As a result, even when the concentration of the target component is the same, the signal detected by the detection unit 102 is stronger than in the case where resonator 106 is not provided, and an improvement in sensitivity is expected.

Note that because the void 163a is provided between the first reflection surface 161a and the first contact surface 162a, which is in contact with the portion of the first holding member in that constitutes the light emitting end of the light emitting unit 101, it is possible to suppress a reduction in the reflection coefficient of the photoacoustic signal at the first reflection surface 161a.

Similarly, because the void 163b, is provided between the second reflection surface 161b and the second contact surface 162b, which is in contact with the detection surface of the detection unit 102, it is possible to suppress a reduction in the reflection coefficient of the photoacoustic signal at the second reflection surface 161b.

Note that if the void 163a and the void 163b are provided as cuboid spaces, it is possible to suppress a reduction in the reflection coefficient of the photoacoustic signal at the first reflection surface 161a and the second reflection surface 161b in the above description, but there is no limitation to this. The first reflection unit 106a and the second reflection unit 106b may be constituted by a porous body such as a sonic crystal, and the voids may be constituted by the porous bodies.

In the second embodiment as well, the area of contact with the measurement site 151 is always kept constant by using the matching member 103, thus making it possible to perform accurate and highly-reproducible photoacoustic measurement.

As described above, according to embodiments of the present invention, the matching member performs acoustic matching with the measurement site by undergoing elastic deformation with a constant elastic modulus, thus making it possible to suppress measurement error caused by body movement when measuring the concentration of a component by photoacoustics.

Note that the present invention is not limited to the embodiments described above, and it is clear that numerous modifications and combinations can be carried out by a person having ordinary knowledge in the art within the technical idea of the present invention.

REFERENCE SIGNS LIST

101 Light emitting unit
101a Light source unit

101b Pulse generation unit
102 Detection unit
103 Matching member
104 Concentration calculation unit
105 Storage unit
111 First holding member
112 Second holding member
113 Coupling portion
114 Optical fiber
115 Optical system
116 Reflection unit
121 Light beam
151 Measurement site.

The invention claimed is:

1. A component concentration measuring device comprising:
    a pair of holding members including a first holding member and a second holding member that are configured to clamp a measurement site of a measurement subject;
    a light emitting device configured to emit a light beam having a wavelength absorbed by a measurement target substance from the first holding member toward the measurement site;
    a detector housed in the second holding member and configured to detect a photoacoustic signal generated by the measurement site when irradiated with the light beam;
    a matching member configured to be arranged between the second holding member and the measurement site, and is configured to perform acoustic matching between the detector and the measurement site by undergoing elastic deformation with a constant elastic modulus while in contact with the measurement site; and
    a resonator configured to cause the photoacoustic signal to resonate, the resonator being constituted by a first reflector that is arranged between the first holding member and the measurement site and has a first reflection surface configured to reflect the photoacoustic signal while allowing the light beam to pass therethrough, and a second reflector that is arranged between the second holding member and the measurement site and has a second reflection surface configured to reflect the photoacoustic signal, wherein the matching member fills a gap between the second reflector and the measurement site when the measurement site is clamped between the pair of holding members, and wherein a distance between the first reflection surface and the second reflection surface is a distance at which the photoacoustic signal resonates;
    wherein:
        the first reflection surface and the second reflection surface are parallel with each other,
        the second reflection surface faces the measurement site, and
        the second reflector includes a second contact surface that faces the second holding member and is in contact with a detection surface of the detector housed in the second holding member, wherein the detection surface faces the measurement site, and a void is disposed between the second reflection surface and the second contact surface.

2. The component concentration measuring device according to claim 1, wherein:
    the first reflection surface faces the measurement site, and the first reflector further includes a first contact surface that faces the first holding member and is in contact with a light emitting end of the light emitting device, and a void is disposed between the first reflection surface and the first contact surface.

3. The component concentration measuring device according to claim 1, wherein:
    the matching member is constituted by a sponge made of a synthetic resin.

4. The component concentration measuring device according to claim 1, wherein:
    the measurement target substance is glucose, and the light emitting device is configured to emit a light beam having a wavelength absorbed by glucose.

5. A method comprising:
    clamping, by a pair of holding members including a first holding member and a second holding member, a measurement site of a measurement subject;
    emitting, by a light emitting device, a light beam having a wavelength absorbed by a measurement target substance from the first holding member toward the measurement site;
    detecting, by a detector, a photoacoustic signal generated by the measurement site when irradiated with the light beam;
    performing, by a matching member, acoustic matching between the detector and the measurement site by undergoing elastic deformation with a constant elastic modulus while in contact with the measurement site; and
    causing, by a resonator, the photoacoustic signal to resonate, the resonator being constituted by a first reflector that is arranged between the first holding member and the measurement site and has a first reflection surface configured to reflect the photoacoustic signal while allowing the light beam to pass therethrough, and a second reflector that is arranged between the second holding member and the measurement site and has a second reflection surface configured to reflect the photoacoustic signal, wherein the matching member fills a gap between the second reflector and the measurement site when the measurement site is clamped between the pair of holding members, and wherein a distance between the first reflection surface and the second reflection surface is a distance at which the photoacoustic signal resonates;
    wherein:
        the first reflection surface and the second reflection surface are parallel with each other,
        the second reflection surface faces the measurement site, and
        the second reflector includes a second contact surface that faces the second holding member and is in contact with a detection surface of the detector housed in the second holding member, wherein the detection surface faces the measurement site, and a void is disposed between the second reflection surface and the second contact surface.

6. The method according to claim 5, wherein the detector is housed in the second holding member.

7. The method according to claim 5, wherein the matching member is disposed between the second holding member and the measurement site while the matching member is performing the acoustic matching between the detector and the measurement site.

8. The method according to claim 5, wherein:
    the first reflection surface faces the measurement site, and the first reflector further includes a first contact surface that faces the first holding member and is in contact with a light emitting end of the light emitting device, and a void is disposed between the first reflection surface and the first contact surface.

9. The method according to claim 5, wherein:

the matching member is constituted by a sponge made of a synthetic resin.

10. The method according to claim 5 further comprising:

obtaining a concentration of the measurement target substance using the photoacoustic signal.

11. The method according to claim 5, wherein:

the measurement target substance is glucose, and the light emitting device emits a light beam having a wavelength absorbed by glucose.

* * * * *